United States Patent [19]

Russell et al.

[11] Patent Number: 5,609,827
[45] Date of Patent: Mar. 11, 1997

[54] BIOPSY SPECIMEN CONTAINER

[75] Inventors: Donald G. Russell, Kensington; Rosemary S. Maxim, Farmington, both of Conn.

[73] Assignee: Beekley Corporation, Bristol, Conn.

[21] Appl. No.: 431,675

[22] Filed: May 2, 1995

[51] Int. Cl.$^6$ ............................... B01L 3/00; A61B 5/00; H05G 1/28
[52] U.S. Cl. ................ 422/102; 422/101; 422/104; 128/771; 604/403; 378/164; 378/208
[58] Field of Search ......................... 422/101, 102, 422/103, 104; 206/438, 569; 128/749, 760, 771; 604/317, 321; 378/164, 208

[56] References Cited

U.S. PATENT DOCUMENTS

| | | | |
|---|---|---|---|
| 3,633,422 | 1/1972 | Grieshaber | 128/771 X |
| 4,092,120 | 5/1978 | Suovaniemi et al. | 23/253 |
| 4,244,920 | 1/1981 | Manschot et al. | 422/102 |
| 4,449,984 | 5/1984 | Cruz | 604/319 |
| 4,557,903 | 12/1985 | McCormick | 422/101 |
| 4,932,791 | 6/1990 | Vetter | 383/93 |
| 5,383,234 | 1/1995 | Russell | 378/164 |
| 5,383,472 | 1/1995 | Devlin et al. | 128/771 |
| 5,424,040 | 6/1995 | Bjornsson | 422/101 |

OTHER PUBLICATIONS

"Radiography of Microcalcifications in Stereotaxic Mammary Core Biopsy Specimens"—Laura Liberman, MD et al (Radiology, Jan. 1994).

"Stereotactically Guided Needle Biopsy of the Breast for Nonpalpable Lesions"—Jay A. Harolds, MD (J Okla State Med. Assoc. vol. 86, Dec. 1993).

Accugrid™—Disposable Specimen Radiograph System With Localizing Grid.

Primary Examiner—Harold Pyon
Attorney, Agent, or Firm—Chilton, Alix & Van Kirk

[57] ABSTRACT

A biopsy specimen container has a bottom surface and an outer wall extending from the bottom surface. A sheet of absorbent material lines the bottom surface. A container cover engages with the outer wall. The cover, wall and bottom define an internal chamber. A divider is mounted within the chamber to form a central compartment and a plurality of peripheral compartments. Radiographically, readable indicia identify each compartment.

17 Claims, 2 Drawing Sheets

BIOPSY SPECIMEN CONTAINER

BACKGROUND OF THE INVENTION

This invention relates to the field of biopsy specimen containers. More specifically, this invention relates to a new and improved container having notable utility in providing for the organization, containment, inspection, radiography and transport of biopsy specimens of breast lesions suspected to be cancerous.

Current mammography frequently identifies tissue densities and/or small calcific deposits which can be interpreted as possibly or probably representing cancer. The suspect areas are usually small and cannot be felt or palpated by the physician. At least two approaches are currently used for investigating the suspect area. In one approach, the suspect area is localized by x-ray examination, a guide wire is implanted in the area, and a block of tissue is then surgically removed. In a second approach, using stereotaxic techniques, the suspect area is localized and then biopsy specimens are obtained by inserting a special hollow needle into and through the suspect area. The core specimens so obtained are typically about 1–1.5 mm in diameter and 10–15 mm in length. It is common practice to obtain an initial core specimen taken through the center of the suspect area. Four or more additional core specimens are taken adjacent to and around the central source location of the initial specimen for a total of at least five specimens. The source location of each specimen relative to the other specimens is recorded for microscopic pathological analysis of the suspect tissue. The relative source locations are needed, for example, when the biopsy is to sample tissue in the are of suspicious calcifications; the specimens are then radiographed to determine which, if any, of the specimens contain any said calcification. Commonly (current practice), each specimen is placed in separate cups or jars for separation, storage and transportation. The many separate specimen cups or jars and the labeling of each cup or jar for identification of the patient and specimen source location can lead to confusion and possible misidentification. If radiography is required, in the cases involving suspicious calcifications, the specimens must be removed from the jar, and placed on a slide or filter paper in order to obtain satisfactory radiographs. This requires further labeling. This handling may result in the loss of some of the tissue and/or displacement of small calcifications.

SUMMARY OF THE INVENTION

The present invention relates to a biopsy specimen container that enables medical personnel to contain, track core site identity, radiograph and transport biopsy specimens safely, quickly and simply. A compartmentalized, sealable container is provided for containing the specimens in a single unit for simultaneously obtaining high detail radiographic analysis of up to five individual cores. Each compartment is visually and radiographically identifiable. The sealable container facilitates adherence to the Universal Precautions prescribed by OSHA for the examination, handling and transportation of body tissue and body liquids. Tissue fixation of the specimens may be provided by the addition of a formalin solution to the container following radiography.

In a preferred embodiment of the invention, a flat, shallow container is provided having a dish-like body and liquid-tight lid. The inside flat bottom of the body is lined with a sheet of absorbent material. A divider segments the internal, flat and shallow chamber of the container into five separate compartments. One compartment is located in the center of the container for the initial, core biopsy directed at the center of the suspicious area. Four peripheral compartments are located around the central compartment at the 3, 6, 9 and 12 o'clock positions. Each peripheral compartment is identified by numerical indicia. The indicia are also radiographically imageable, therefore maintaining identity of the site of the biopsy specimens. The lid seals the container body to provide a liquid-tight enclosure which conforms to OSHA protocol for handling body liquids and body tissues.

Before using the container, the bottom sheet of absorbent material is saturated with a sterile saline solution. Any excess liquid is poured from the container. The saline solution serves to maintain cell integrity in an isotonic environment. The thin, uniform layer of water provided by the saturated sheet of absorbent material provides modest, uniform attenuation of the x-ray beam and helps avoid overexposure and "burn out" of tissue detail and the x-ray image of small calcific deposits.

For core needle biopsy investigation of a suspected area of a breast (e.g., where a mass or suspicious calcifications are imaged on mammography), a first core specimen is removed from the center of the suspect area and placed in the central compartment. Four or more additional core specimens are removed, by adjustment of the stereotaxic guide, from locations adjacent to and around the central location of the initial core specimen. These additional biopsies, by convention, are taken at locations, in accord with a clock face at 12, 3, 6 and 9 o'clock. Each additional specimen is placed in a peripheral appropriately labelled compartment corresponding to the specimen's relative location around the suspect area. The container lid is then installed to provide a liquid-tight container.

The entire container, with lid installed, can then radiographed. This is, preferably, magnified, ×1.5 or ×2, radiographically. The diameter of the container has been selected to permit the entire container to be imaged within the field covered by the commonly used magnification x-ray beam. (This field is 7–10 cm in diameter.) Each radiograph shows all five specimens and their locations in relation to the central suspect area. Each radiograph also shows the compartments and the compartment indicia showing the relative source locations of the specimens. After completion of the x-ray analysis, the lid may be removed and a preservative, commonly formalin, may be placed in the container to fix the tissue samples in a manner leading to further pathological and microscopic examination.

It is an object of the present invention to provide a new and improved biopsy specimen container for separating, identifying, containing and transporting multiple specimens as a single unit.

It is another object of the invention to provide a new and improved core tissue specimen container for maintaining core specimens in the same relative positions as their core site locations at the center of and around a suspect area under investigation.

It is still another object of the invention to provide a tissue specimen container that facilitates simultaneous radiographic analysis of related biopsy specimens.

It is yet another object of the invention to provide a biopsy specimen container which provides radiograph indicia showing the relative source locations of the specimens in the suspect area.

It is another object of the invention to permit a radiographic magnification view of the entire container and all of the core samples in one exposure.

It is, furthermore, an object of this invention to provide a uniform and reproducible layer of water density to permit a standard radiographic technique for the production of consistent, highly detailed, appropriately exposed radiographs.

It is also an object of this invention to provide a layer of water for a modest and uniform attenuation of the x-ray energy to avoid "burn-out" of tissue detail and/or loss of the radiographic image of minute calcifications.

It is a further object of the invention to provide for quality assurance and on-going check on the accuracy of the core needle sampling system. Separation of samples with site tracking can be achieved by consistent use in all stereotaxic biopsies. When this is combined with specific microscopic analysis of each core and respective individual reports, there is a record affirming accurate sampling.

It is a further object of the invention to provide a biopsy specimen container which facilitates adherence to OSHA standards for handling body liquids and body tissues.

These and other objects of the invention can be readily understood from the following specification and accompanying drawings.

DETAILED DESCRIPTION OF THE DRAWINGS

Figure 1:
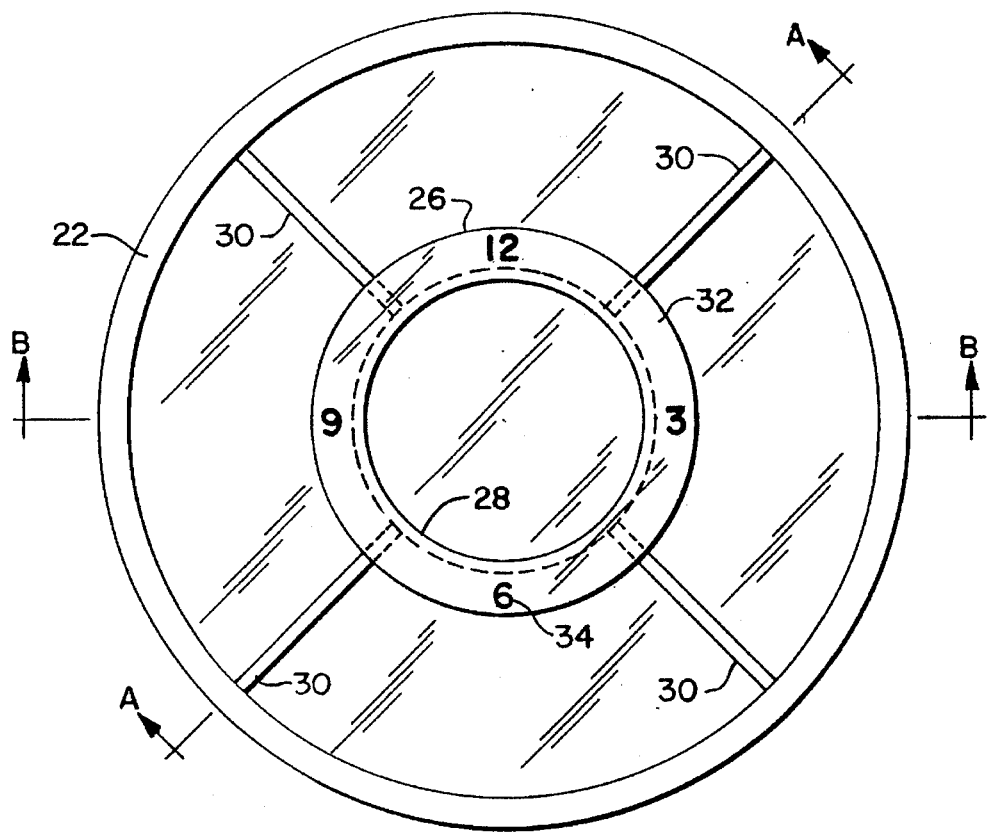
FIG. 1 is a top plan view of a container incorporating a first embodiment of the invention, showing the container with the container lid removed.
Figure 2:
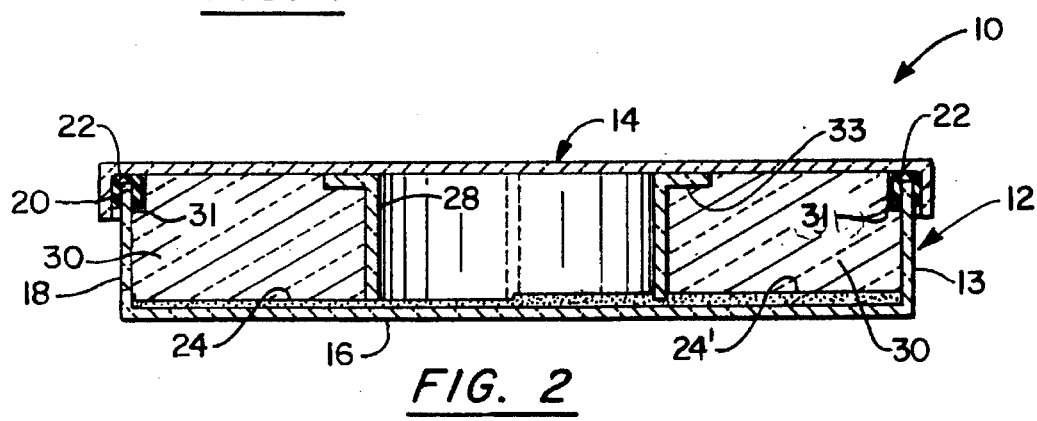
FIG. 2 is an elevation section view of the container taken generally along line A—A of FIG. 1, showing the container with the container lid installed.
Figure 3:
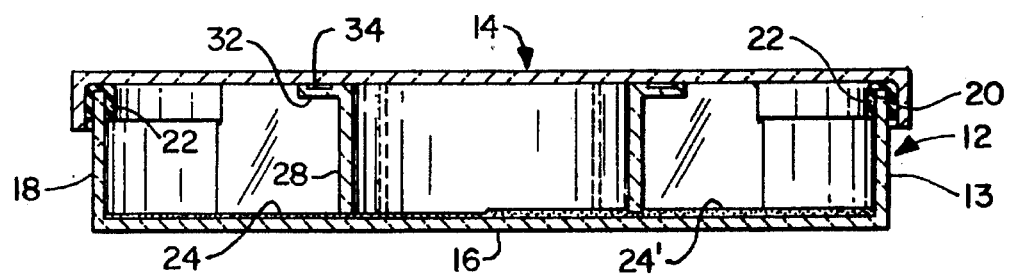
FIG. 3 is an elevation section view of the container taken generally along line B—B of FIG. 1, also showing the container with the container lid installed.

In the figures, like numerals are used to represent the same or like parts. A biopsy specimen container 10 incorporating a first embodiment of the invention is shown in FIGS. 1–3.

The container 10 is flat and shallow and has a generally petri-dish-shaped body 12 and a lid 14. The body 12 comprises a plastic body 13 and a circular, upper edge seal 22. The lid 14 is made entirely of plastic. The body 12 has a flat bottom 16 and a short, upright, outer circular wall 18. The body 12 has an external diameter of approximately 9 cm. The outer circular wall 18 has a height of approximately 1.5 cm. The container 10 is sufficiently small to be positioned entirely within the field covered by the x-ray beam of an x-ray machine of the type commonly employed for mammography magnification utilizing projections.

The circular seal 22 has a U-shaped, transverse cross section and is made of a suitable resilient material such as rubber. The seal is mounted on the upper circular edge 20 of the plastic body 13 and forms the upper edge of the outer wall 18. A depending peripheral lip or flange of the lid 14 is press fit over the resilient seal 22 to firmly retain the lid on the container body 12 and seal the internal chamber. The seal 22 forms an impervious, liquid-tight seal between the lid 14 and body 12 to provide for the safe handling of body tissues and body liquids. If the container is inverted, the contents of the container will not escape. A container may be provided without the seal 22 by providing a suitable tight press fit or threaded connection between the lid and upper edge of the plastic body. Flanges may be molded projecting inward from the inner wall of the container. These will permit the divider to be held securely in place so that it is not moved or dislodged during handling and/or during the removal of the cover.

The inside flat bottom 16 of the container is covered by a circular support sheet or pad 24 of absorbent material, preferably made of suitable paper. A small amount of saline solution is added to the container to saturate the support sheet 24. Excess liquid is poured from the container; otherwise, the excess liquid which is relatively dense at the low kilovoltage of 23–24 KV commonly employed in breast specimen radiography can obscure radiographic detail of the specimens deposited within the container. The absorbent support sheet 24 also helps disperse excess liquid from the biopsy specimens and furthermore, maintains the specimens in a moist isotonic state preserving cell integrity. The absorbent sheet is shown in FIGS. 2 and 3 in the dry state (identified by the numeral 24) and in the saturated state (identified by the numeral 24').

Disposed within the body 12 is a one-piece, plastic insert or divider 26. The insert 26 divides the internal chamber into five separate compartments or chambers for respective biopsy specimens deposited on the bottom support sheet 24. The insert 26 rests on the bottom support sheet 24 so as not to restrict the distribution of saline solution or other liquid from one compartment to another compartment through the absorbent medium 24.

The insert 26 has a central circular divider wall 28 which forms a central circular compartment. The circular wall 28 is coaxial with and has a diameter slightly greater than one-third the diameter of the container body 12. The insert 26 has four radial divider fins or walls 30 which extend radially outwardly from the circular wall 28 to and in engagement with the outer wall 18. The insert 26 divider may be securely held rotationally and laterally by flanges projecting inward from the inner container wall. Four separate, substantially identical compartments are formed by the radial walls 30, outer wall 18 and central circular wall 28. The one-piece insert 26 is held snugly in place between the opposed flat surfaces of the Container lid 12 and bottom support sheet 24 and preferably by a friction engagement with the outer wall 18 and/or by the flanges 27 projecting from the container wall. If the container 10 is inverted, the insert 26 retains the specimens within their respective compartments. The radial walls 30 have notches 31 at their top, outer corners to receive the upper edge seal 22 for positively retaining the insert 26 within the container body 12 when the lid 14 is removed.

A flat, indicia bearing ring or rim 32 is provided at the top of the central circular wall 28. The indicia ring 32 is integrally molded with the rest of the insert 26 or is separately formed and cemented to the top edges of the circular wall 28 and radial walls 30. The radial walls 30 have notches 33 at their top inner corners for receiving the indicia ring 32.

Numeral indicia 34 are provided on the indicia ring 32 to identify the four peripheral compartments. In the preferred embodiment, the numeral indicia 34 identify the positions of the peripheral compartments relative to the central compartment, by identifying the 3, 6, 9 and 12 o'clock positions of the compartments. The indicia are engraved on the indicia bearing ring 32, preferably to a depth of 1–1.5 mm so that they appear on a radiograph due to the difference in density between the air within the engraved indicia and the surrounding plastic of the ring 32. The indicia are also clearly visible to the operator to allow correct placement of the core specimen in accord with biopsy site location. In the alternative, the indicia (or the ring area surrounding the indicia) are printed on the ring 32 with a radio-opaque substance so that the indicia appear on a radiograph.

To facilitate visual inspection of the biopsy specimens, the plastic body 13, lid 14 and insert 26 are preferably transparent. To facilitate radiographic analysis, the plastic body 13, lid 14 and insert 26 are constructed of an appropriate low density radiolucent material which has a modest and uniform attenuation of the x-ray energy and which will not therefore obscure radiographic detail.

Figure 4:
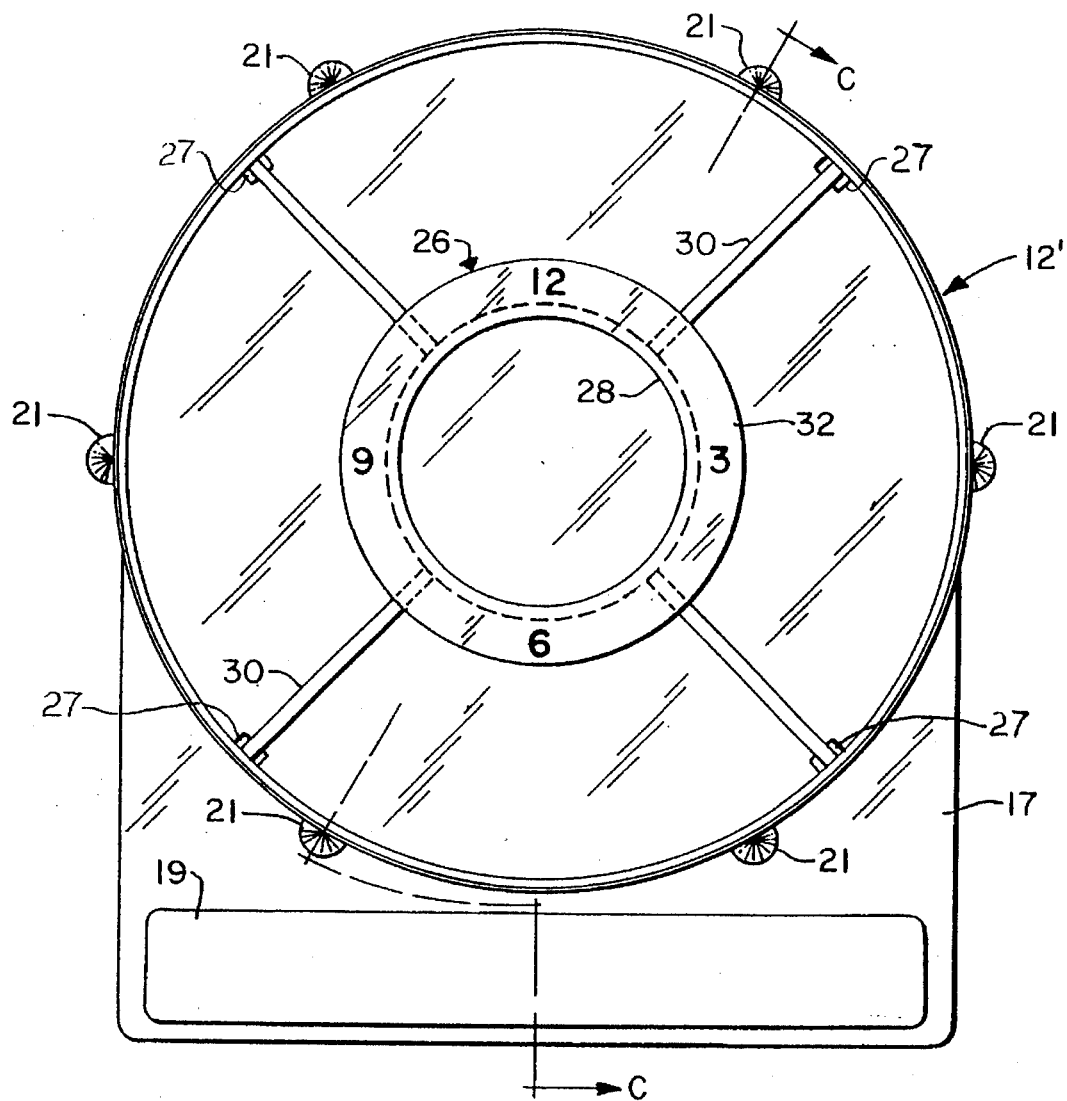
FIG. 4 is a top plan view of a container incorporating a second embodiment of the invention, showing the container with the container lid removed.
Figure 5:
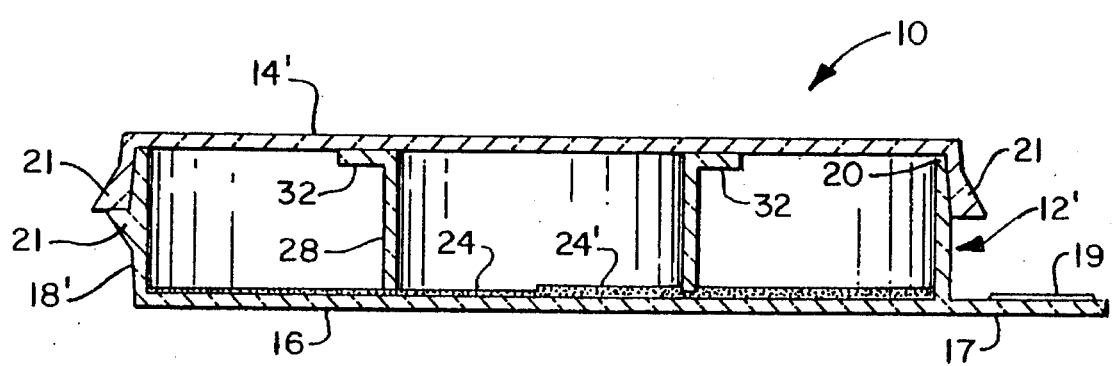
FIG. 5 is an elevation section view of the container shown in FIG. 4, taken generally along line C—C of FIG. 4, showing the container with the container lid installed.

An alternative embodiment 10' is shown in FIGS. 4 and 5. The embodiment 10' is identical to the embodiment 10 shown in FIGS. 1–3 except as hereinafter described. The flat bottom 16' of the container 10' has a flat external extension 17 at the 6 o'clock position. A paper label 19 is mounted on the upper flat face of the extension 17 to provide a writing surface for patient and specimen identification. An alternative use of this extension would be the use as a site for the application of the commonly used adhesive printed patient identification label. Applied to this extension, the label will not interfere with the inspection of the samples or be the source of spurious radiographic shadows. The extension 17 is preferably at least 1 inch by 3 inches to provide a sufficient area for attachment of the printed patient identification label.

The lid 14' and outer wall 18' are designed to seal the container 10' without the sealing ring 22. The opposed mating surfaces of the lid 14' and outer wall 18' are tapered upwardly and inwardly very slightly to form the desired liquid-tight seal when the lid 14' is press fit on the container body 12'. The outer, generally cylindrical, surfaces of the lid 14' and outer wall 18' are formed with small tabs or projections 21 to facilitate installation and removal of the lid 14'. The outer wall projections 18' serve as stops for establishing the fully installed position of the lid, 14'. As in the embodiment of FIGS. 1–3, the divider 26' is snugly retained between the opposed, inside flat surfaces of the lid 14' and bottom support sheet 24.

In either container, 10 or 10' additional flanges 27 may be molded into the interior of the outer wall 18 to prevent rotation of the divider 26 within the container. Such additional flanges 27 can supplement or replace a friction fit of the divider 26 with the outer wall 18.

When using the container 10 or 10', a core specimen taken from the center of a suspect area, is placed in the central compartment of the container. Up to four additional core specimens are placed in the outer compartments corresponding to the relative source locations of the specimens in the suspect area. The lid is secured to the top of the body and, in the embodiment 10', appropriate patient and specimen identification is recorded on the identification label 19.

The entire container 10 or 10' is preferably sterilized before use to reduce possible contamination of the core specimen needle. The needle can then contact the inside of the sterilized container without contaminating the needle and so that a single needle may be used for the entire core biopsy procedure when multiple biopsies are obtained. Approximately 5 ml of sterile saline solution is added to the bottom support sheet 24 before the biopsy specimens are deposited in the container. Excess solution is poured from the container after the bottom sheet is saturated. The saturated bottom sheet serves to attenuate the commonly used low energy x-rays thus avoiding image burnout of microcalcification and tissue detail. The absorbent material also serves to absorb and disperse any excess body liquid from the biopsy specimens.

X-ray analysis of the core specimens is then performed with the biopsy specimens in the sealed container. The numeral indicia will appear on the radiograph to indicate the source location of each specimen relative to the central core specimen in a direct and easily understood manner. The short, upright outer wall of the container and the short upright divider walls of the insert will show on the x-ray radiograph along with the ring indicia to aid in identifying and distinguishing the five container compartments.

After radiography of the biopsy specimens, the container can be partly filled with a liquid preservative such as formalin or formaldehyde sufficient to cover the specimens. The container is then resealed with the lid. Formalin is a toxic substance and personnel exposure to the substance is prevented by the closed container.

While preferred embodiments of the foregoing invention have been set forth for purposes of illustration, the foregoing description should not be deemed a limitation of the invention. Accordingly, various modifications, adaptations and alternatives may occur to one skilled in the art without departing from the spirit and scope of the present invention.

What is claimed is:

1. A biopsy specimen container comprising:

a container body having a bottom with an inside bottom support surface;

a container cover adapted to be installed on the container body to form with the container body an internal, flat and shallow containment chamber;

a bottom support sheet of absorbent material on the bottom support surface;

a divider within the internal chamber having a plurality of upstanding wall portions dividing the internal chamber between the bottom sheet and cover into a plurality of separate compartments for a plurality of biopsy specimens to be deposited on the bottom support sheet;

and compartment identifying means for identifying the compartments in a radiograph of the container.

2. The biopsy specimen container of claim 1 wherein said compartment identifying means identify the relative source locations of biopsy specimens deposited on the bottom support sheet.

3. The biopsy specimen container of claim 1 wherein the container body has an upstanding outer wall with a resilient upper edge seal engageable by the cover when the cover is installed to seal the internal chamber.

4. The biopsy specimen container of claim 1 wherein the plurality of separate compartments include a central compartment and a plurality of peripheral compartments surrounding the central compartment.

5. The biopsy specimen container of claim 1 wherein the container body has an upstanding outer wall and wherein the bottom of the container has a flat external section extending outwardly from the outer wall.

6. The biopsy specimen container of claim 5 wherein the flat external section provides a writing surface for patient and specimen identification.

7. A biopsy specimen container comprising:

a container body having a bottom with an inside generally flat bottom support surface and an outer wall extending upright from said bottom and defining a container opening;

a container cover adapted to be installed on the outer wall of the container body to cover the container opening and form with the container body an internal containment chamber;

a bottom support sheet of absorbent material on the bottom support surface;

a divider insert mounted within the internal chamber between the bottom sheet and cover, said insert having a plurality of upstanding wall portions extending between the bottom sheet and cover for dividing the internal chamber into a plurality of separate compartments for a plurality of biopsy specimens to be deposited on the bottom support sheet;

and radiographically readable indicia for identifying said compartments.

8. The biopsy specimen container of claim 7 wherein the upstanding divider wall portions comprise a central divider wall forming a central compartment within the internal chamber and a plurality of radial divider walls extending between the central divider wall and outer wall and forming with the central wall and outer wall a plurality of peripheral compartments surrounding the central compartment; and the central divider wall and radial divider walls extending between the bottom support sheet and cover.

9. The biopsy specimen container of claim 8 wherein the indicia are engraved indicia.

10. The biopsy specimen container of claim 7 wherein the outer wall has an upper edge seal engageable by the cover to seal the internal chamber when the cover is installed.

11. The specimen container of claim 7 wherein the outer wall has a plurality of external projections to facilitate installation of the cover on the outer wall.

12. A biopsy specimen container comprising:

a container body having a radiographically translucent bottom and a radiographically identifiable outer wall extending upright a predetermined distance away from the bottom to define an internal, flat and shallow containment chamber above the bottom and within the outer wall;

a cover adapted to be installed on the container body;

radiographically identifiable divider wall means having a plurality of upstanding wall portions extending upright for said predetermined distance away from the bottom for dividing the internal containment chamber into a plurality of separate compartments for a plurality of biopsy specimens to be deposited therein; and radiographically identifiable indicia for identifying the relative source locations of the plurality of biopsy specimens deposited in the compartments.

13. The biopsy specimen container of claim 12 further comprising a sheet of absorbent material on the bottom of the container body.

14. The biopsy specimen container of claim 12 wherein the divider wall means divides the internal containment chamber into a central compartment and a plurality of peripheral compartments surrounding the central compartment.

15. The biopsy specimen container of claim 12 wherein the bottom has an external section extending outwardly from the outer wall.

16. The biopsy specimen container of claim 15 wherein the external bottom section provides a writing surface.

17. The biopsy specimen container of claim 12 further comprising flange means for holding said divider wall means in a fixed position relative to said outer wall.

\* \* \* \* \*